United States Patent [19]

Bourzat et al.

[11] Patent Number: 4,576,954
[45] Date of Patent: Mar. 18, 1986

[54] ANTI-RHEUMATIC 5-(SUBSTITUTED AMINO)-1,2-DITHIOL-3-ONE COMPOUNDS AND THEIR USE

[75] Inventors: Jean-Dominique Bourzat; Claude Cotrel, both of Paris; Daniel Farge, Thiais; Jean-Marc Paris, Vaires S/Marne; Gérard Taurand, Creteil, all of France

[73] Assignee: Phone-Poulenc Sante, Courbevoie, France

[21] Appl. No.: 582,043

[22] Filed: Feb. 21, 1984

[30] Foreign Application Priority Data

Feb. 24, 1983 [FR] France ................................ 83 03005

[51] Int. Cl.$^4$ .................... A61K 31/47; C07D 215/02; C07D 217/02
[52] U.S. Cl. .................................... 514/314; 514/312; 546/139; 546/141; 546/142; 546/143; 546/144; 546/145; 546/146; 546/147; 546/148; 546/152; 546/153; 546/155; 546/156; 546/159; 549/33
[58] Field of Search .............. 424/258; 546/139, 141, 546/142, 143, 144, 145, 146, 147, 148, 152, 153, 155, 156, 159

[56] References Cited

U.S. PATENT DOCUMENTS

| 3,657,437 | 4/1972 | Bader | 424/248 |
| 3,772,273 | 11/1973 | Gilbert | 544/353 |
| 3,890,319 | 6/1975 | Danielewicz | 544/353 |
| 3,984,405 | 10/1976 | Krapcho | 544/105 |
| 4,207,318 | 6/1980 | Rowlands | 544/105 |
| 4,254,118 | 3/1981 | Gauthier | 544/105 |
| 4,273,773 | 6/1981 | Demerson | 548/482 |
| 4,464,300 | 8/1984 | Borer | 260/239 BB |
| 4,477,378 | 10/1984 | Gold | 260/239 BB |

OTHER PUBLICATIONS

United States Patent Quarterly, vol. 197, p. 543, ex parte Lewis, Miller & Law.

Primary Examiner—Donald G. Daus
Assistant Examiner—Robert Benson
Attorney, Agent, or Firm—Stevens, Davis, Miller & Mosher

[57] ABSTRACT

New derivatives of the general formula (I) in which:
R=H or Cl and either $R_1$ and $R_2$ form a tetrahydroquinoxaline, tetrahydroquinoline, tetrahydroisoquinoline, dihydrobenzoxazine, tetrahydro-1H-benzazepine or isoindoline ring, it being possible for all these rings to be substituted by one or more halogen, carboxyl, alkoxycarbonyl, carbamoyl, alkylcarbamoyl, dialkylcarbamoyl, trifluoromethyl, cyano, nitro, alkoxy, alkylthio or alkyl, substituted by carboxyl, alkoxycarbonyl, carbamoyl, alkylcarbamoyl, dialkylcarbamoyl, hydroxyl, amino, alkylamino or dialkylamino, or $R_1$=alkyl and $R_2$=alkyl substituted by phenyl which is itself unsubstituted or substituted by one or more halogen, alkyl, alkoxy, alkylthio, hydroxy, amino, alkylamino, dialkylamino, carboxy, alkoxycarbonyl, carbamoyl, alkylcarbamoyl, dialkylcarbamoyl, trifluoromethyl, cyano or nitro, all the alkyls having 1 to 4 C in a straight or branched chain.

These new products are used as antirheumatics.

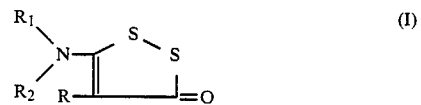

5 Claims, No Drawings

ANTI-RHEUMATIC 5-(SUBSTITUTED AMINO)-1,2-DITHIOL-3-ONE COMPOUNDS AND THEIR USE

The present invention provides 5-amino-1,2-dithiol-3-one compounds of the formula:

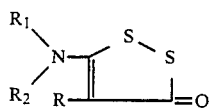

in which R represents a hydrogen or chlorine atom and either $R_1$ and $R_2$, together with the nitrogen atom to which they are bonded, form a 1,2,3,4-tetrahydroquinoxaline, 1,2,3,4-tetrahydroquinoline, 1,2,3,4-tetrahydroisoquinoline, 3,4-dihydro-1,4-2H-benzoxazine, 2,3,4,5-tetrahydro-1H-benzazepine or isoindoline ring each being substituted or unsubstituted by one or more halogen atoms, carboxyl, alkoxycarbonyl, carbamoyl, alkylcarbamoyl, dialkylcarbamoyl, trifluoromethyl, cyano, nitro, alkoxy, alkylthio and alkyl radicals, substituted or unsubstituted by a carboxyl, alkoxycarbonyl, carbamoyl, alkylcarbamoyl, dialkylcarbamoyl, hydroxyl, amino, alkylamino or dialkylamino radical, or $R_1$ represents an alkyl radical and $R_2$ represents an alkyl radical which is substituted by a phenyl radical which is itself unsubstituted or substituted by one or more halogen atoms or alkyl, alkoxy, alkylthio, hydroxy, amino, alkylamino, dialkylamino, carboxy, alkoxycarbonyl, carbamoyl, alkylcarbamoyl, dialkylcarbamoyl, trifluoromethyl, cyano or nitro radicals, each of the aforesaid alkyl radicals and alkyl portions hereinbefore or hereinafter mentioned containing 1 to 4 carbon atoms in a straight or branched chain, and, where they exist, their acid addition salts, their metal salts and their addition salts with nitrogen bases.

5-Amino-4-chloro-1,2-dithiol-3-ones are already known from German Pat. Nos. 1,242,324 (equivalent to GB 1136793) and 1,278,701 (equivalent to U.S. Pat. No. 3659010) and from Certificate of Addition No. 94,485 to French Pat. No. 1,498,374; neither of these documents either disclose products according to the invention or suggest a therapeutic application for this type of product.

According to the invention, compounds of formula (I) in which R is a chlorine atom and the other symbols are as defined above can be prepared by reacting an amine of formula:

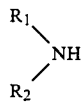

in which $R_1$ and $R_2$ are as defined above, with 4,5-dichloro-1,2-dithiol-3-one of the formula:

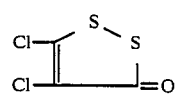

The reaction is in general carried out in an organic solvent, such as an alcohol, for example methanol or dimethylformamide, in the presence of a slight excess, based on the theoretical amount, of an acid acceptor, such as an alkali metal carbonate or bicarbonate, for example potassium carbonate or bicarbonate, or an organic base, for example nitrilo-tris(propan-2-ol), at a temperature from 0° to 80° C., preferably at about 20° C.

4,5-Dichloro-1,2-dithiol-3-one of the formula (III) can be prepared in accordance with the method of F. BOBERG, Ann. Chem. 681, 169 (1965).

Amines of the formula (II) can be prepared by utilisation or adaptation of the known methods of the prior art, with which those skilled in the art are familiar.

According to the invention, compounds of formula (I) in which R is a hydrogen atom and the other symbols are as defined above can be prepared by dechlorination of a product of formula (I) in which R is a chlorine atom and the other symbols are as defined above, i.e. a compound of the formula:

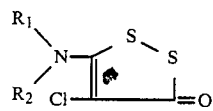

The dechlorination can be carried out by any method known to those skilled in the art for carrying out this reaction without affecting the remainder of the molecule. It is particularly advantageous to carry out the dechlorination with the aid of a trialkyl-tin hydride, for example tributyl-tin hydride, at a temperature from 0° to 40° C.

Compounds of formula (I) can be purified by conventional known methods, e.g. by crystallization, chromatography or, where appropriate, successive extractions in an acid and basic medium.

Compounds of formula (I) in which the substituents $R_1$ and $R_2$ carry an amino function, such as is defined above, can optionally be converted into acid addition salts by the action of an acid in an organic solvent, such as an alcohol, a ketone, an ester or chlorinated solvent. The salt precipitates, if appropriate after concentration of its solution and it is separated off by filtration or decantation.

In an analogous manner, compounds of formula (I) in which the substituents $R_1$ and $R_2$ carry an acid function, such as is defined above, can optionally be converted into metal salts or addition salts with nitrogen bases.

In order to carry out the processes according to the invention which are described above, it may be necessary to introduce protective groups for the functions present in the molecule of the reactants in order to avoid secondary reactions before one or other of the processes according to the invention is carried out. It will then be possible to preserve or remove the protective grouping, depending on whether the product obtained is a product according to the invention or not. Thus, if an amine function is present in the molecule, it is necessary to protect this function, e.g. by a tert.-butoxycarbonyl radical, and to liberate the amine function in an acid medium (e.g. with the aid of an aqueous hydrochloric acid solution or, preferably, an acetic acid solution of hydrogen chloride gas). Similarly, if a hydroxyl function (alcohol or carboxylic acid) is present in the molecule, this function may be protected in the form of an ether or ester; the initial function can be regenerated by conventional techniques known to those skilled in the art.

Compounds according to the invention and, where these exist, their salts have useful pharmacological properties which render them capable of being used in the treatment of rheumatic disease. They have proved to be active at concentrations of about $5 \times 10^{-6}$M in the test for measurement of activation of macrophages in vitro in accordance with the method of J. SCHNYDER and M. BAGGIOLINI (J. Exp. Med. 148, 1449, 1978).

In addition, compounds of formula (I) have a low toxicity. Their $LD_{50}$ is in general above 900 mg/kg on single oral administration to mice.

Compounds of formula (I) which are of particular interest are those in which R represents a chlorine atom and either $R_1$ and $R_2$, together with the nitrogen atom to which they are bonded, form a 1,2,3,4-tetrahydroquinoxaline, 1,2,3,4-tetrahydroquinoline, 1,2,3,4-tetrahydroisoquinoline, 3,4-dihydro-1,4-2H-benzoxazine, 2,3,4,5-tetrahydro-1H-benzazepine or isoindoline ring, each being substituted or unsubstituted by an alkyl group, or $R_1$ is an alkyl radical and $R_2$ is an alkyl radical which is substituted by a phenyl radical.

Example of compounds of particular interest are:
4-chloro-5-(4-methyl-1,2,3,4-tetrahydroquinoxalin-1-yl)-1,2-dithiol-3-one-3-one;
4-chloro-5-(1,2,3,4-tetrahydroquinolyl)-1,2-dithiol-3-one;
4-chloro-5-(3,4-dihydro-1,4-2H-benzoxazine-4-yl)-dithiol-3-one;
4-chloro-5-(1,2,3,4-tetrahydroisoquinol-2-yl)-1,2-dithiol-3-one;
4-chloro-5-(isoindolin-2-yl)-1,2-dithiol-3-one;
4-chloro-5-(2,3,4,5-tetrahydro-1H-benz[d]azepin-3-yl)-1,2-dithiol-3-one;
4-chloro-5-[N-methyl-N-(2-phenylethyl)-amino]-1,2-dithiol-3-one; and
4-chloro-5-(N-benzyl-N-methylamino)-1,2-dithiol-3-one.

For medicinal use, the products according to the invention can be used per se or, in the form of pharmaceutically acceptable salts, i.e. salts which are non-toxic at the doses used.

Examples of pharmaceutically acceptable salts are addition salts with mineral acids, such as hydrochlorides, sulphates, nitrates or phosphates, or with organic acids, such as acetates, propionates, succinates, benzoates, fumarates, maleates, methanesulphonates, isothionates, theophylline-acetates, salicylates, phenolphthaleinates, and methylene-bis-β-hydroxynaphthoates, and substitution derivatives of these compounds or with alkali metals, such as sodium, potassium or lithium, or with alkaline earth metals, such as calcium or magnesium, or organic bases, such as ethanolamine salts and lysine salts.

The examples below show how the invention can be applied in practice.

EXAMPLE 1

A suspension of potassium bicarbonate (5.5 g) in a solution of 4,5-dichloro-1,2-dithiol-3-one (9.35 g) and 1-methyl-1,2,3,4-tetrahydroquinoxaline (8.14 g) in methanol (75 cc) is stirred at a temperature of about 20° C. for 20 hours. The insoluble product is separated off by filtration, washed 3 times with methanol (30 cc in total) and 5 times with distilled water (100 cc in total) and dried in air at a temperature of about 20° C. After recrystallization from acetonitrile, 4-chloro-5-(4-methyl-1,2,3,4-tetrahydroquinoxalin-1-yl)-1,2-dithiol-3-one (10.3 g) of m.p. 132° C. is obtained.

1-Methyl-1,2,3,4-tetraquinoxaline can be prepared in accordance with the method described by R. F. SMITH, W. J. REBEL and T. H. BEACH, J. Org. Chem., 24, 205, (1959).

EXAMPLE 2

The procedure followed is analogous to that described in Example 1, but 4,5-dichloro-1,2-dithiol-3-one (9.35 g) and 1,2,3,4-tetrahydroquinoline (7.3 g) are used as starting substances, and, after recrystallization from acetonitrile, 4-chloro-5-(1,2,3,4-tetrahydroquinolyl)-1,2-dithiol-3-one (8.9 g) of m.p. 120° C. is obtained.

EXAMPLE 3

The procedure followed is analogous to that described in Example 1, but 4,5-dichloro-1,2-dithiol-3-one (11.2 g) and 3,4-dihydro-1,4-2H-benzoxazine (8.9 g) are used as starting substances, and, after recrystallization from acetonitrile, 4-chloro-5-(3,4-dihydro-1,4-2H-benzoxazine-4-yl)-1,2-dithiol-3-one (10.2 g) of m.p. 143° C. is obtained.

3,4-Dihydro-1,4-2H-benzoxazine can be prepared by the method described by H. SHIRAI, T. HAYAZAKI and H. YASUO, Chem. Abstr. 73 25378 g.

EXAMPLE 4

The procedure followed is analogous to that described in Example 1, but 4,5-dichloro-1,2-dithiol-3-one (9.3 g) and 1,2,3,4-tetrahydroisoquinoline (7.3 g) are used as starting substances, and, after recrystallization from acetonitrile, 4-chloro-5-(1,2,3,4-tetrahydroisoquinol-2-yl)-1,2-dithiol-3-one (10.8 g) of m.p. 114° C. is obtained.

EXAMPLE 5

The procedure followed is analogous to that described in Example 1, but 4,5-dichloro-1,2-dithiol-3-one (7.8 g) and isoindoline (5 g) are used as starting substances, and, after recrystallization from dioxane, 4-chloro-5-(isoindolin-2-yl)-1,2-dithiol-3-one (6.9 g) of m.p. 194° C. is obtained.

Isoindoline can be prepared in accordance with the method described by J. BORNSTEIN, S. C. LASHUA and A. P. BOISELLE, J. Org. Chem. 22, 1255 (1957).

EXAMPLE 6

The procedure followed is analogous to that described in Example 1, but 4,5-dichloro-1,2-dithiol-3-one (3.16 g) and 2,3,4,5-tetrahydro-1H-benz[d]azepine (2.5 g) are used as starting substances, and, after recrystallization from acetonitrile, 4-chloro-5-(2,3,4,5-tetrahydro-1H-benz[d]azepin-3-yl)-1,2-dithiol-3-one (2.3 g) is obtained in the form of an ochre powder of m.p. 141° C.

2,3,4,5-Tetrahydro-1H-benz[d]azepine can be prepared in accordance with the method described by P. RUGGLI, B. B. BUSSEMAKER, W. MÜLLER and A. STAUB, Helv. Chim. Acta, 18, 1388 (1935).

EXAMPLE 7

Potassium bicarbonate (6 g) and a solution of N-methylphenethylamine (8 g) in methanol (150 cc) are added to a solution of 4,5-dichloro-1,2-dithiol-3-one (11.2 g) in methanol (350 cc). The reaction mixture is stirred at a temperature of about 20° C. for 20 hours, filtered and concentrated to dryness under reduced pressure (2.7 kPa) at 40° C. The residue is dissolved in methylene chloride (210 cc); the solution obtained is washed 3 times with distilled water (60 cc in total), dried over magnesium sulphate, filtered and concentrated to dryness under reduced pressure (2.7 kPa) at 40° C. The crystals obtained are recrystallized from a mixture of isopropyl ether and ethyl acetate (75/25 by volume); 4-chloro-5-[N-methyl-N-(2-phenylethyl)-amino]-1,2-dithiol-3-one (5.3 g) is thus obtained in the form of yellow crystals of m.p. 75° C.

EXAMPLE 8

The procedure followed is analogous to that described in Example 7, but 4,5-dichloro-1,2-dithiol-3-one (11.7 g) and N-methylbenzylamine (7.6 g) are used as starting substances, and a crude oily product (15.6 g) is obtained. This product is dissolved in methylene chloride (50 cc) and the solution obtained is poured onto silica gel (450 g) in a column 6 cm in diameter. The column is first eluted with a mixture of cyclohexane and ethyl acetate (70/30 by volume) (2.7 liters); the corresponding eluate is removed. The column is then eluted with the mixture used above (3.5 liters); the corresponding eluate is concentrated to dryness under reduced pressure (0.13 kPa) at 20° C. 4-Chloro-5-(N-benzyl-N-methylamino)-1,2-dithiol-3-one (12.3 g) is thus obtained in the form of a yellow oil [Rf=0.36); thin layer chromatography on silica gel; eluant cyclohexane/ethyl acetate (70/30 by volume)].

The present invention also relates to the medicaments consisting of at least one compound of the formula (I) in the free form or in the form of pharmaceutically acceptable acid addition salts, metal salts or addition salts with a base, in the pure state or in the form of a composition in which it is associated with any other pharmaceutically compatible product, for example diluents or adjuvants, which can be inert or physiologically active. The medicaments according to the invention can be administered orally, parenterally, rectally or topically.

Tablets, pills, powders (in particular in gelatine capsules or in cachets) or pellets can be used as solid compositions for oral administration. In these compositions, the compound according to the invention is mixed with one or more inert diluents, such as starch, cellulose, sucrose, lactose or silica. These compositions can also include substances other than diluents, e.g. one or more lubricants, such as magnesium stearate or talc, a colourant, a coating (coated tablets) or a lacquer.

Solutions, suspensions, emulsions, syrups and pharmaceutically acceptable elixirs containing inert diluents such as water, ethanol, glycerol, vegetable oils or paraffin oil, can be used as liquid compositions for oral administration. These compositions can also include substances other than diluents, e.g. wetting, sweetening, thickening, flavouring or stabilising products.

The sterile compositions for parenteral administration are preferably aqueous or non-aqueous solutions, or suspensions or emulsions. Examples of solvents are: water, propylene glycol, a polyethylene glycol, vegetable oils, in particular olive oil, injectable organic esters, e.g. ethyl oleate, or other suitable organic solvents. These compositions can also contain adjuvants, in particular wetting agents, agents for imparting isotonicity, emulsifiers, dispersants and stabilisers. Sterilisation can be carried out in several ways, e.g. by filtration under aseptic conditions, by incorporating sterilising agents into the composition, by irradiation or by heating. The compositions can also be prepared in the form of sterile solid compositions which can be dissolved in an injectable sterile medium at the time of use.

The compositions for rectal administration are suppositories or rectal capsules, which, in addition to the active product, contain excipients such as cacao butter, semi-synthetic glycerides or polyethylene glycols.

The compositions for topical application can be, e.g., creams, ointments, lotions, eye lotions, mouthwashes, nose drops or aerosols.

In human therapy, the compounds according to the invention are particularly useful in the treatment of rheumatic disease.

The doses depend on the desired effect and the duration of the treatment; for an adult, they are generally between 50 and 1000 mg per day, administered orally, in one or more individual doses.

The physician will determine the posology which he considers to be most appropriate, as a function of the age, the weight and all the other factors peculiar to the subject to be treated.

The example which follows illustrates a composition according to the invention.

EXAMPLE

Tablets containing 50 mg doses of active compound and having the following composition are prepared by the usual technique:

| | |
|---|---|
| 4-chloro-5-(1,2,3,4-tetrahydroisoquinol-2-yl)-1,2-dithiol-3-one | 50 mg |
| starch | 60 mg |
| Lactose | 50 mg |
| magnesium stearate | 2 mg |

We claim:

1. A 5-amino-1,2-dithiol-3-one compound of the formula

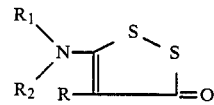

in which R represents a hydrogen or chlorine atom and $R_1$ and $R_2$, together with the nitrogen atom to which they are bonded, form a 1,2,3,4-tetrahydroquinoline or 1,2,3,4-tetrahydroisoquinoline ring, each being substituted or unsubstituted by a halogen atom, carboxyl, alkoxycarbonyl, carbamoyl, alkylcarbamoyl, dialkylcarbamoyl, trifluoromethyl, cyano, nitro, alkoxy, alkylthio or alkyl radical substituted or unsubstituted by a carboxyl, alkoxycarbonyl, carbamoyl, alkylcarbamoyl, dialkylcarbamoyl, hydroxyl, amino, alkylamino or dialkylamino radical, each of the aforesaid alkyl radicals and alkyl portions hereinbefore mentioned containing 1 to 4 carbon atoms in a straight or branched chain, and, where they exist, its pharmaceutically acceptable acid addition salts, its pharmaceutically acceptable metal salts and its pharmaceutically acceptable addition salts with nitrogen bases.

2. A compound according to claim 1 in which R is a chlorine atom and $R_1$ and $R_2$, together with the nitrogen atom to which they are bonded, form a 1,2,3,4-tetrahydroisoquinoline or ring, each being substituted or unsubstituted by an alkyl group.

3. A compound according to claim 1 which is 4-chloro-5-(1,2,3,4-tetrahydroisoquinol-2-yl)-1,2-dithiol-3-one or its pharmaceutically acceptable acid addition salts.

4. A pharmaceutical composition useful for treating rheumatic disease which contains at least one compound according to claim 1 together with one or more compatible and pharmaceutically acceptable diluents or adjuvants.

5. A method of treating rheumatic disease which comprises administering to a subject suffering therefrom or liable thereto an effective amount of a compound according to claim 1.

* * * * *